United States Patent [19]

Galli Angeli et al.

[11] Patent Number: 5,234,927
[45] Date of Patent: Aug. 10, 1993

[54] SOLID PHARMACEUTICAL COMPOSITION FOR ORAL ADMINISTRATION CONTAINING DAPIPRAZOLE

[75] Inventors: Depalmo Galli Angeli, Falconara; Leandro Baiocchi, Rome, both of Italy

[73] Assignee: Aziende Chimiche Riunite Angelini Francesco A.C.R.A.F. S.p.A., Rome, Italy

[21] Appl. No.: 917,153

[22] Filed: Jul. 20, 1992

[30] Foreign Application Priority Data

Jul. 24, 1991 [IT] Italy .................. MI91 A 002044

[51] Int. Cl.[5] .................. A61K 31/495; A61K 31/50
[52] U.S. Cl. .................. 514/253; 514/970; 424/692
[58] Field of Search ................. 514/253, 970; 424/692

[56] References Cited

U.S. PATENT DOCUMENTS

| | | | |
|---|---|---|---|
| 4,755,385 | 7/1988 | Etienne et al. | 424/687 |
| 4,879,294 | 11/1989 | Schoenwald | 514/253 |
| 5,041,446 | 8/1991 | Silvestrini | 514/255 |
| 5,093,132 | 3/1992 | Makino et al. | 514/970 |

FOREIGN PATENT DOCUMENTS

| | | | |
|---|---|---|---|
| 0288659 | 11/1988 | European Pat. Off. | |
| 1209634 | 10/1970 | United Kingdom | 424/692 |
| 2020269 | 11/1979 | United Kingdom | |

OTHER PUBLICATIONS

Chemical Abstract 101 (15): 122508w 1984.
Aoki et al., Chemical Abstracts–CA113(8):65275q, 1990.

Primary Examiner—S. J. Friedman
Assistant Examiner—William Jarvis
Attorney, Agent, or Firm—Ladas & Parry

[57] ABSTRACT

A stable solid pharmaceutical composition for oral administration comprising dapiprazole or a physiologically acceptable acid salt thereof together with a pharmaceutically acceptable inert excipient and magnesium oxide as a degradation retarding agent is disclosed.

6 Claims, No Drawings

SOLID PHARMACEUTICAL COMPOSITION FOR ORAL ADMINISTRATION CONTAINING DAPIPRAZOLE

DESCRIPTION

This invention relates to an improved solid pharmaceutical composition for oral administration containing dapiprazole. More specifically, it relates to an improved solid pharmaceutical composition for oral administration having improved stability.

It is known that dapiprazole is preferably administered in the form of an acid addition salt with a physiologically acceptable organic and inorganic acid.

Dapiprazole hydrochloride of the formula

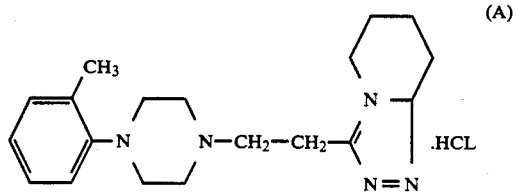

is the most extensively investigated salt in the clinical field; it is an adrenolytic drug, disclosed in the Italian Patent No. 1.094.076, granted on the Jul. 26, 1985, and is currently employed in collyria.

The above mentioned Italian Patent prognosticates two further therapeutic employments for dapiprazole hydrochloride, i.e. withdrawl syndrome and schizophrenia, which would imply the availability of pharmaceutical dosage unit forms suitable for systemic administration, preferably for oral administration.

However, the solid pharmaceutical dosage units prepared up to now proved to be very poor in stability due to the quick degradation of dapiprazole.

The mechanism and reasons for this degradation of dapiprazole hydrochloride are unknown. However, we have found that the degradation rate of dapiprazole hydrochloride results in the formation of secondary amines; perhaps, o-tolyl-piperazine, hereinafter referred to as "o.tp". Furthermore, we have found that the progress of the degradation can be monitored by means of the colorimetric reaction of H. Karwich and Carl H. Meyers (Anal. Chemistry 51, 319 (1979)) as modified by K. S. Tung and D. H. Harweik (Anal. Chem. 52, 1387 (1980)).

Assuming that one molecule of o.tp is formed from every molecule of dapiprazole which degrades, the percent degradation of the dapiprazole will be calculated by means of the following formula:

$$\% \text{ degradation} = \% \text{ o.tp} \times \text{dapiprazole MWt/o.tp MWt}$$

wherein MWt means molecular weight.

Finally, we have now unexpectedly found that the degradation of dapiprazole in the granulates for the manufacture of solid pharmaceutical dosage units for oral use is prevented or substantially reduced by addition of a suitable amount of magnesium oxide.

Therefore, it is an object of this invention to provide an improved solid pharmaceutical composition for oral administration consisting of or made from a granulate comprising dapiprazole or a physiologically acceptable acid addition salt thereof and at least one pharmaceutically acceptable inert, solid excipient, wherein the improvement comprises adding to said granulate a level of magnesium oxide capable of preventing or substantially reducing the degradation of dapiprazole or of the acid addition salt thereof.

Preferably, the pharmaceutical composition according to this invention comprises a physiologically acceptable acid addition salt of dapiprazole. Dapiprazole hydrochloride is the preferred acid addition salt.

The amount of magnesium oxide which prevents or substantially reduces the degradation of dapiprazole, preferably as hydrochloride salt, is substantially higher than the one which is added when this ingredient is conventionally employed as a glidant agent.

Indeed, magnesium oxide is conventionally employed in the preparation of pharmaceutical granulates in order to improve the flowability of the powders (glidant agent); in such an employment magnesium oxide is often associated with an equivalent weight of silica. The total amount of magnesium oxide as a glidant agent in the granulates is of from 1 to 3% (w/w); higher amounts of magnesium oxide are known to cause the opposite effect, i.e. they reduce the flowability of the powders.

Preferably, the minimum level of magnesium oxide in the granulates of the present invention is of 10% (w/w).

The granulates of this invention are prepared according to conventional techniques which comprise mixing, kneading, granulating, sieving, drying and the like.

In the present description and in the appended claims the term "granulate" is used to mean that portion of the pharmaceutical dosage unit which is in close contact with dapiprazole hydrochloride. In addition to dapiprazole hydrochloride and magnesium oxide, the granulate of this invention comprise at least one pharmaceutically acceptable inert, solid excipient such as lactose, corn starch, microcrystalline cellulose, mannitol, and the like. Furthermore, the granulate of the invention may comprise pharmaceutically useful additives such as, for example, aggregants, disaggregants, sweeteners, colouring agents, thickening agents, lubricants, and the like. Typical examples of said additives are hydroxy propyl methyl cellulose as a thickening agent, polyethylene glycols and magnesium stearate as lubricants, and sodium carboxy methyl amido as a disaggregating agent.

The person skilled in the art will appreciate that some pharmaceutical dosage units such as, for instance, tablets and soluble powders, are formed by the granulate only. The minimum level of magnesium oxide in these pharmaceutical dosage units will, therefore, be of 10% (w/w).

However, in other pharmaceutical dosage units such as, for instance, sugar coated tablets, film coated tablets, hard gelatin capsules and soft gelatin capsules, the granulate forms a more or less substantial portion of the total weight of the pharmaceutical dosage unit.

In such a case the minimum level of magnesium oxide in the pharmaceutical dosage unit will obviously be as lower than the above mentioned 10% (w/w) minimum level in the granulate, as low is the portion of the granulate in the whole pharmaceutical dosage unit. For example, when the weight of the granulate amounts to 50% (w/w) of the total weight of the pharmaceutical dosage unit, the minimum level of magnesium oxide in the pharmaceutical dosage unit of this invention will be of 5% (w/w).

Therefore, it is a further object of this invention to provide an improved pharmaceutical dosage unit for oral administration manufactured from a granulate containing dapiprazole or a physiologically acceptable acid addition salt thereof and at least one pharmaceutically acceptable inert, solid excipient, wherein the improvement consists in that said granulate contains a level of magnesium oxide capable of preventing or substantially reducing the degradation of dapiprazole or of the acid addition salt thereof.

Preferably, the pharmaceutical dosage unit according to this invention is manufactured from a granulate containing a physiologically acceptable acid addition salt of dapiprazole. Even more preferably the above acid addition salt is the hydrochloride and the minimum level of magnesium oxide in the granulate is of 10% (w/w).

The pharmaceutical dosage units according to this invention are manufactured according to well known methods comprising conventional techniques such as tabletting, sugar coating, film coating, filling, and the like.

Table I shows that magnesium oxide at the level of 3% (w/w) in the granulate does not satisfactory prevent degradation of dapiprazole hydrochloride whereas a satisfactory increase in the stability of the active ingredient is obtained when the level of magnesium oxide in the granulate is of at least 10% (w/w).

TABLE I

| Granulate | Additive | % (w/w) | Time (days) | T °C. | % o.tp | % degradation |
|---|---|---|---|---|---|---|
| A | — | — | 15 | 70° C. | 9.76 | 20.04 |
| B | MgO | 3.29 | 15 | 70° C. | 2.13 | 4.37 |
| C | MgO | 6.33 | 15 | 70° C. | 0.22 | 0.44 |
| D | MgO | 11.9 | 15 | 70° C. | 0.13 | 0.27 |
| E | MgO | 21.28 | 15 | 70° C. | 0.099 | 0.20 |

The person skilled in the art will easily select the maximum level of magnesium oxide depending on the desired preventing action on the degradation of dapiprazole, the volume of the desired pharmaceutical dosage unit and the known pharmacological action of magnesium oxide per se. For example, in the preparation of a tablet comprising 1 mg of dapiprazole hydrochloride salt, a granulate containing more than 0.65% of magnesium oxide has been successfully utilized (see example 8).

Further experiments have been carried out in order to evaluate whether other metal oxides, such as aluminum oxide, and other alkalizing agents, such as magnesium carbonate behave like magnesium oxide. The results are reported in Table II showing that the action of magnesium oxide is rather unique.

TABLE II

| Granulate | Substance added | % | Time days | T° C. | % o.tp | % degradation |
|---|---|---|---|---|---|---|
| F | MgCO₃ | 21.28 | 15 | 70° C. | 2.570 | 5.28 |
| G | AL₂O₃ | 21.28 | 15 | 70° C. | 1.500 | 3.08 |
| H | MgO | 21.28 | 15 | 70° C. | 0.099 | 0.20 |

The composition of the granulates from A to H (see Tables I and II above) are given hereinbelow; they are not intended to limit the present invention in any way.

100 g of granulate contain:

| Example 1 | Granulate A |
|---|---|
| Dapiprazole HCL | 2.70 g |
| Lactose | 75.30 g |
| Microcrystalline cellulose | 13.51 g |

| -continued | |
|---|---|
| Hydrogenated castor oil | 5.41 g |
| Magnesium stearate | 1.62 g |
| Sodium carboxymethylamido | 1.14 g |
| Colloidal silica | 0.32 g |
| Example 2 | Granulate B |
| Dapiprazole HCL | 2.61 g |
| Lactose | 72.82 g |
| Microcrystalline cellulose | 13.07 g |
| Magnesium oxide | 3.29 g |
| Hydrogenated castor oil | 5.23 g |
| Magnesium stearate | 1.57 g |
| Sodium carboxymethylamido | 1.10 g |
| Colloidal silica | 0.31 g |
| Example 3 | Granulate C |
| Dapiprazole HCL | 2.53 g |
| Lactose | 70.53 g |
| Microcrystalline cellulose | 12.66 g |
| Magnesium oxide | 6.33 g |
| Hydrogenated castor oil | 5.06 g |
| Magnesium stearate | 1.52 g |
| Sodium carboxymethylamido | 1.06 g |
| Colloidal silica | 0.30 g |
| Example 4 | Granulate D |
| Dapiprazole HCL | 2.38 g |
| Lactose | 66.34 g |
| Microcrystalline cellulose | 11.9 g |
| Magnesium oxide | 11.9 g |
| Hydrogenated castor oil | 4.76 g |
| Magnesium stearate | 1.43 g |
| Sodium carboxymethylamido | 1.00 g |
| Colloidal silica | 0.29 g |
| Example 5 | Granulate E |
| Dapiprazole HCL | 2.13 g |
| Lactose | 59.28 g |
| Microcrystalline cellulose | 10.64 g |
| Magnesium oxide | 21.28 g |
| Hydrogenated castor oil | 4.25 g |
| Magnesium stearate | 1.28 g |
| Sodium carboxymethylamido | 0.89 g |
| Colloidal silica | 0.25 g |
| Example 6 | Granulate F |
| Dapiprazole HCL | 2.13 g |
| Lactose | 59.28 g |
| Microcrystalline cellulose | 10.64 g |
| Magnesium oxide | 21.28 g |
| Hydrogenated castor oil | 4.25 g |
| Magnesium stearate | 1.28 g |
| Sodium carboxymethylamido | 0.89 g |
| Colloidal silica | 0.25 g |
| Example 7 | Granulate G |
| Dapiprazole HCL | 2.13 g |
| Lactose | 59.28 g |
| Microcrystalline cellulose | 10.64 g |
| Alluminum hydroxide | 21.28 g |
| Hydrogenated castor oil | 4.25 g |
| Magnesium stearate | 1.28 g |
| Sodium carboxymethylamido | 0.89 g |
| Colloidal silica | 0.25 g |
| Example 8 | Granulate H |
| (useful for 1 mg tablets of dapiprazole.HCL) | |
| Dapiprazole HCL | 2.38 g |
| Lactose | 11.90 g |
| Microcrystalline cellulose | 11.90 g |
| Magnesium oxide | 66.33 g |
| Hydrogenated castor oil | 4.76 g |
| Magnesium stearate | 1.43 g |
| Sodium carboxymethylamido | 1.00 g |
| Colloidal silica | 0.29 g |

We claim:

1. An improved solid pharmaceutical composition for oral administration consisting of or made from a granulate comprising dapiprazole or a physiologically acceptable acid addition salt thereof and at least one pharmaceutically acceptable inert, solid excipient, wherein the improvement comprises adding to said granulate a level of magnesium oxide capable of preventing or substantially reducing the degradation of dapiprazole or of the acid addition salt thereof.

2. An improved pharmaceutical composition according to claim 1, wherein said acid addition salt is dapiprazole hydrochloride.

3. An improved pharmaceutical composition according to claim 1 wherein the minimum level of magnesium oxide in the granulate is of 10% (w/w).

4. An improved pharmaceutical dosage unit for oral administration manufactured from a granulate containing dapiprazole or a physiologically acceptable acid addition salt thereof and at least one pharmaceutically acceptable inert, solid excipient, wherein the improvement consists in that said granulate contains a level of magnesium oxide capable of preventing or substantially reducing the degradation of dapiprazole or of the acid addition salt thereof.

5. An improved pharmaceutical dosage unit according to claim 4, wherein the acid addition salt is dapiprazole hydrochloride.

6. An improved pharmaceutical dosage unit according to claim 4, wherein the minimum level of magnesium oxide in the granulate is of 10% (w/w).

* * * * *